US010420741B2

(12) United States Patent
Saito et al.

(10) Patent No.: US 10,420,741 B2
(45) Date of Patent: Sep. 24, 2019

(54) MEGALIN ANTAGONIST

(71) Applicants: EA Pharma Co., Ltd., Chuo-ku (JP); Niigata University, Niigata-shi (JP)

(72) Inventors: Akihiko Saito, Niigata (JP); Nobumasa Aoki, Niigata (JP); Yoshihisa Hori, Tokamachi (JP); Shoji Kuwahara, Niigata (JP); Michihiro Hosojima, Sanjo (JP); Hiroshi Iwata, Kawasaki (JP); Saori Matsuda, Kawasaki (JP)

(73) Assignees: EA Pharma Co., Ltd., Chuo-ku (JP); Niigata University, Niigata-shi (JP)

( * ) Notice: Subject to any disclaimer, the term of this patent is extended or adjusted under 35 U.S.C. 154(b) by 193 days.

(21) Appl. No.: 15/216,225

(22) Filed: Jul. 21, 2016

(65) Prior Publication Data

US 2016/0324813 A1 Nov. 10, 2016

Related U.S. Application Data

(63) Continuation of application No. PCT/JP2015/051718, filed on Jan. 22, 2015.

(30) Foreign Application Priority Data

Jan. 24, 2014 (JP) ................................ 2014-011530

(51) Int. Cl.

| | |
|---|---|
| ***A61K 31/19*** | (2006.01) |
| ***A61K 33/24*** | (2019.01) |
| ***A61K 31/198*** | (2006.01) |
| ***A61K 45/06*** | (2006.01) |
| ***A61K 38/12*** | (2006.01) |
| ***A61K 38/14*** | (2006.01) |
| ***A61K 31/436*** | (2006.01) |
| ***B65D 81/32*** | (2006.01) |

(52) U.S. Cl.

CPC .......... *A61K 31/198* (2013.01); *A61K 31/436* (2013.01); *A61K 33/24* (2013.01); *A61K 38/12* (2013.01); *A61K 38/14* (2013.01); *A61K 45/06* (2013.01); *B65D 81/32* (2013.01)

(58) Field of Classification Search

CPC .............................. A61K 31/198; A61K 33/24

See application file for complete search history.

(56) References Cited

U.S. PATENT DOCUMENTS

| | | | |
|---|---|---|---|
| 2005/0119346 | A1 | 6/2005 | Kumar et al. |
| 2011/0165264 | A1 | 7/2011 | Tejedor Jorge et al. |
| 2014/0018293 | A1 | 1/2014 | Delano et al. |
| 2016/0367642 | A1 | 12/2016 | Delano et al. |

FOREIGN PATENT DOCUMENTS

| | | | |
|---|---|---|---|
| DE | 100 53 506 | A1 | 5/2002 |
| JP | 2003-261459 | A | 9/2003 |
| WO | WO 97/37649 | A1 | 10/1997 |
| WO | WO 98/20836 | A2 | 5/1998 |
| WO | WO 03/018544 | A1 | 3/2003 |
| WO | WO 2012/045083 | A2 | 4/2012 |

OTHER PUBLICATIONS

Staph Infection [online] {retrieved on Apr. 10, 2008 from the Internet} {URL: http://www.medicinenet.com/script/main/art.asp?articlekey=1991 &pf=3&page2}.*

Salmonellosis [online] [retrieved on Feb. 27, 2009] and retrieved from URL; http://www.cdc.gOv/nczved/dfbmed/diseaseJisting/salmonellosis_gi.html#4.*

International Search Report dated Mar. 31, 2015, in PCT Application No. PCT/JP2015/051718, filed Jan. 22, 2015.

Marzolo et al., Biological Research, 2011 vol. 44, pp. 89 to 105.

Christensen et al., Nature Reviews Molecular Cell Biology, 2002 , vol. 3, pp. 258 to 268.

Schmitz et al., Journal of Biological Chemistry, 2002, vol. 277, pp. 618-622.

Motoyoshi et al., Kidney International, 2008, vol. 74, 10, pp. 1262 to 1269.

Orlando et al., Proceedings of the National Academy of Sciences of the United States of America, 1992, vol. 89, 15, pp. 6698 to 6702.

Ministry of Health, Labor and Welfare, "To all medical personnel", [Online], 2006 Ministry of Health, Labor and Welfare website, Topics, [Searched on Dec. 2, 2014], Internet <URL:http://www.mhlw.go.jp/topics/2006/11/dl/tp1122-1p03.pdf>.

Mikihisa Takano, "Development of aminoglycoside nephrotoxicity reduction formulation targeting receptor molecules", [Online], Jan. 2005, Hiroshima University Graduate School of Biomedical Sciences, Public Relations Committee, Hiroshima Bimes News No. 5, p. 6, [Searched on Dec. 2, 2014], Internet <URL:http://www.hiroshimau.ac.jp/bimes/BiMeSNews/Research/pdb6096.html>.

Makiko Kusama et al . , "Cilastatin ni yoru Vancomycin Jin Shogai Keigen Sayo no Seirigaku-teki Kaiseki", Jpn J Clin Pharmacol Ther, 2000, 31(2), pp. 315 to 316.

Tamehisa Ishida et al., "Ofloxacin Taisei Coagulase Insei Budo Kyukin ni yori Shojita Hakunaisho Jutsugo Kyokakumaku Kansen no Ichirei", Japanese Journal of Clinical Ophthalmology, 1998, 52(10), pp. 1695 to 1698.

Hiroyuki Okamoto et al., "A Case of Werner Syndrome with Endophthalmitis Onset 10 Years after Cataract Surgery", Dokkyo Journal of Medical Sciences, 2013, 40(3), pp. 185 to 188.

Akihiko Saito et al., "Megalin, a Multiligand Endocytotic Receptor: The Role in the Development of Diabetic Nephropathy, Metabolic Syndrome-related Nephropathy and Uremia", Niigata Medical Journal, 2005, 119(1), pp. 1 to 9.

Extended European Search Report dated Jul. 5, 2017 in Patent Application No. 15740494.8.

Takahiro Suzuki et al. "Megalin Contributes to Kidney Accumulation and Nephrotoxicity of Colistin", Antimicrobial Agents and Chemotherapy, vol. 57, No. 12, XP055383833, Dec. 1, 2013, pp. 6319-6324.

Ernest M. Walker et al., "Nephrotoxic and Ototoxic Agents", Clinical Toxicology, Clinics in Laboratory Medicine, vol. 10, No. 2, XP055384977, Jun. 1990, pp. 323-354.

* cited by examiner

*Primary Examiner* — Shawquia Jackson

(74) *Attorney, Agent, or Firm* — Oblon, McClelland, Maier & Neustadt, L.L.P.

(57) ABSTRACT

The present invention includes cilastatin or a pharmaceutically acceptable salt thereof as an active component and a suppressant for renal impairment or inner ear disorders, induced via megalin by at least one megalin ligand which is selected from the group consisting of polymyxins, aminoglycoside antibiotics, glycopeptide antibiotics, cisplatin, and pharmaceutically acceptable salts thereof.

11 Claims, 8 Drawing Sheets

MEGALIN ANTAGONIST

TECHNICAL FIELD

The present invention relates to a megalin antagonist, which antagonizes a megalin ligand by binding to megalin, and a pharmaceutical composition which contains the megalin antagonist.

Priority is claimed on Japanese Patent Application No. 2014-011530, filed Jan. 24, 2014, the content of which is incorporated herein by reference.

BACKGROUND ART

Megalin is a cell membrane protein also known as Low Density Lipoprotein (LDL) receptor-related protein 2 (LRP-2) or Glycoprotein 330 (gp 330) and is a large membrane-type single transmembrane-type glycoprotein with a molecular weight of approximately 600 KDa. Megalin has an extracellular region having four functional domains on the N-terminal side, a short intracellular region on the C-terminal side, and a single cell transmembrane region between the two. Megalin functions as an endocytosis receptor and takes in substances (megalin ligands) which bind to the extracellular region thereof into the cell. The expression of megalin in the bodies of mammals has been confirmed in the kidney proximal tubule epithelial cells (primarily, the luminal membrane), the inner ear epithelial cells, the testes, the neural ectoderm, and the like. In particular, in the kidney proximal tubule epithelial cells, glomerular filtered proteins, administered drugs, or the like bind to the extracellular region of megalin and are taken into the cell by endocytosis (for example, refer to NPL 1 and 2). For example, in the kidney proximal tubule epithelial cells, megalin-mediated endocytosis has a function of preventing physical decline by reabsorbing biological factors in the kidney proximal tubule.

A large number of biological factors, drugs, and the like have been reported as megalin ligands. Specific reported examples include albumin, aminoglycosides, amylase, angiotensin II, angiotensin 1-7, apolipoprotein B, apolipoprotein E, apolipoprotein H, apolipoprotein J (Clusterin), apolipoprotein M, aprotinin, bone morphogenetic protein 4, calcium ions, cathepsin B, coagulation factor VIII, connective tissue growth factor (CTGF), cytochrome C, cystatin C, epidermal growth factor (EGF), folate binding protein, galactosidase A, gelsolin, hemoglobin, insulin, insulin-like growth factor I (IGF-I), lactoferrin, leptin, lipoprotein lipase, liver-type fatty acid binding protein, Lp (a), lysozyme, metallothionein, α1-microglobulin, β2-microglobulin, myoglobin, neutrophil gelatinase associated lipocalin (NGAL), odorant binding proteins, parathyroid hormones, pancreatitis associated protein 1 (PAP-1), plasminogen, plasminogen activator inhibitor type 1 (PAI-1), plasminogen activator inhibitor type 1 urokinase (uPAI-1), plasminogen activator inhibitor type 1 tissue plasminogen activator (tPAI-1), polymyxin B, prolactin, pro-urokinase, recombinant activated factor VIIa (rFVIIa), retinol binding protein (RBP), selenoprotein p, seminal vesicle secreted protein II, sex hormone-binding globulin, sonic hedgehog protein, thyroglobulin, transcobalamin-vitamin B12, transthyretin, trichosanthin, vitamin d-binding protein, or the like (for example, refer to NPL 3).

These drugs and metabolites thereof may cause severe renal impairment. There are a variety of routes in the pathogenesis of renal impairment; however, the reabsorption mechanism through megalin is known to be one factor. For example, polymyxin B of the polymyxins, which are cyclic peptide antibiotics, has been shown to cause cell damage by being taken into the cell by endocytosis after binding to megalin. In addition, aminoglycoside antibiotics such as gentamicin are taken into the cell by endocytosis after binding to megalin; however, it is reported that an effect of suppressing nephrotoxicity caused by gentamicin aminoglycoside antibiotics is obtained by co-administration of lysozyme, aprotinin, and cytochrome C, which are megalin ligands (for example, refer to PTL 1).

There are cases in which renal impairment is caused by biological factors. It is known that, in a situation where an excess of albumin is discharged in primary urine and the reabsorption function due to megalin is pathologically increased, the kidney proximal tubular cells are damaged, which leads to chronic renal impairment such as diabetic nephropathy. In addition, for example, in NPL 4, when the kidney glomerular epithelial cells (podocytes) are destroyed by the administration of LMB2, which is an immunotoxin, to cause filtration function failure, the renal tubular cells are damaged by cellular stress as a result of albumin discharged in large amounts in primary urine being excessively taken into the cells via megalin; however, it is reported that such cell damage does not occur in renal tubular cells in which megalin is not expressed in a megalin mosaic-type knockout mouse (that is, a mouse where only a part of the megalin expression in the renal tubular cells is lacking).

On the other hand, cilastatin (cilastatin; (Z)-7-[[(R)-2-amino-2-carboxyethyl] thio]-2-[[[(S)-2,2-dimethylcyclopropyl] carbonyl] amino]-2-heptenoic acid) has an inhibitory activity with respect to dehydropeptidase-I (DHP-I), which is a metabolic enzyme present in the kidney proximal tubule brush border membrane. Anti-microbial activity is not recognized in cilastatin; however, since the carbapenem-based antibiotic imipenem is subject to degradation by DHP-I and the metabolites thereof greatly damage the kidney proximal tubule, mixtures of imipenem and cilastatin are used as injectable solutions with the object of preventing renal impairment due to these metabolites.

PTL 2 reports that cilastatin has an effect of attenuating the toxicity of drugs having a number of nephrotoxicities. The same document reports that, in practice, when cisplatin, which is an anti-cancer drug, is co-administered with cilastatin to rats, the nephrotoxicity was improved, and shows that cilastatin has the possibility of reducing the nephrotoxicity by inhibiting the transport path into the cells via cholesterol rafts.

On the other hand, it is widely known that inner ear disorders (tinnitus, dizziness, and hearing loss) are caused as a side effect of using certain types of antibiotics (aminoglycoside drugs such as gentamicin, and glycopeptide anti-microbial agents such as vancomycin) and anti-cancer drugs such as cisplatin (NPL 6).

In addition, it is known that many agents which cause inner ear disorders function as megalin ligands and that megalin is localized in the inner ear epithelial cells (NPL 7).

CITATION LIST

Patent Literature

[PTL 1] Japanese Unexamined Patent Application, First Publication No. 2003-261459

[PTL 2] United States Patent Application, Publication No. 2011/0165264

Non-Patent Literature

[NPL 1] Marzolo et al., Biological Research, 2011, Vol. 44, pages 89 to 105.

[NPL 2] Christensen et al., Nature Reviews Molecular Cell Biology, 2002, Vol. 3, pages 258 to 268.

[NPL 3] Schmitz et al., Journal of Biological Chemistry, 2002, Vol. 277, pages 618 to 622.

[NPL 4] Motoyoshi et al., Kidney International, 2008, Vol. 74, No. 10, pages 1262 to 1269.

[NPL 5] Orlando et al., Proceedings of the National Academy of Sciences of the United States of America, 1992, Vol. 89, No. 15, pages 6698 to 6702.

[NPL 6] Ministry of Health, Labor and Welfare, "To all medical personnel", [Online], 2006 Ministry of Health, Labor and Welfare website, Topics, [Searched on Dec. 2, 2014], Internet <URL: http://www.mhlw.go.jp/topics/2006/11/dl/tp1122-1p03.pdf>

[NPL 7] Mikihisa Takano, "Development of aminoglycoside nephrotoxicity reduction formulation targeting receptor molecules", [Online], January 2005, Hiroshima University Graduate School of Biomedical Sciences, Public Relations Committee, HIROSHIMA BIMES NEWS No. 5, page 6, [Searched on Dec. 2, 2014], Internet <URL: http://www.hiroshima-u.ac.jp/bimes/BiMeSNews/Research/pdb6096.html>

SUMMARY OF INVENTION

Technical Problem

Regarding the megalin ligands for which there is a concern that uptake into cells will cause cell damage, it is possible to suppress the uptake thereof into the cells by suppressing the binding to megalin and to expect a resulting direct attenuation in cell damage.

The present invention has an object of providing a compound or pharmaceutically acceptable salts thereof which can effectively suppress the binding of megalin to megalin ligands, a megalin antagonist which includes the above compound or pharmaceutically acceptable salts thereof as an active component, a suppressant of nephrotoxicity or inner ear disorders caused by megalin ligands, which includes the above compound or pharmaceutically acceptable salts thereof, a pharmaceutical composition including the above compound or pharmaceutically acceptable salts thereof, and a therapy combining the above compound or pharmaceutically acceptable salts thereof with megalin ligands.

Solution to Problem

As a result of intensive research to solve the problems described above, the present inventors found that cilastatin binds to megalin and can antagonize megalin ligands (in the present specification, in a case of simply referring to "megalin ligands", unless otherwise stated, the term "megalin ligand" refers to a megalin ligand other than cilastatin), that, for example, colistin (also referred to as polymyxin E) functions as a megalin ligand and can cause renal impairment (also referred to as nephrotoxicity in the present specification) via megalin, and that renal impairment due to colistin is improved by the co-administration of colistin and cilastatin, thereby completing the present invention.

In addition, the present inventors also discovered that, since cilastatin can antagonize megalin ligands, cilastatin can effectively suppress not only renal impairment caused by megalin ligands, but also inner ear disorders, thereby completing the present invention.

That is, the present invention provides the following megalin ligand antagonists [1] to [9] and a pharmaceutical composition.

[1] A megalin ligand antagonist including cilastatin or a pharmacologically acceptable salt thereof as an active component.

[2] The megalin ligand antagonist according to [1], which is for use in suppressing cell damage caused by megalin ligands being excessively taken into a cell.

[3] The megalin ligand antagonist according to [2], which is for use in preventing or treat renal impairment.

[4] The megalin ligand antagonist according to any one of [1] to [3], which is co-administered with a megalin ligand to an animal.

[5] The megalin ligand antagonist according to any one of [2] to [4], in which the megalin ligand is one or more selected from the group consisting of polymyxins, aminoglycoside antibiotics, glycopeptide antibiotics, and cisplatin.

[6] A pharmaceutical composition including the megalin ligand antagonist of any one of [1] to [5].

[7] The pharmaceutical composition of [6] further including a megalin ligand as an active component.

[8] The pharmaceutical composition of [7], in which the megalin ligand is a substance which causes cell damage by being excessively taken into a cell.

[9] The pharmaceutical composition of [7], in which the megalin ligand is one or more selected from the group consisting of polymyxins, aminoglycoside antibiotics, and glycopeptide antibiotics.

That is, the present invention has the following aspects.

(1) A suppressant of renal impairment or inner ear disorders induced via megalin by at least one megalin ligand which is selected from the group consisting of polymyxins, aminoglycoside antibiotics, glycopeptide antibiotics, cisplatin, tacrolimus, and pharmaceutically acceptable salts thereof, the suppressant including cilastatin or a pharmaceutically acceptable salt thereof as an active component.

(2) The suppressant according to (1), which is a suppressant for inner ear disorders.

(3) The suppressant according to (1) or (2), in which the megalin ligand is at least one megalin ligand which is selected from the group consisting of colistin, colistin methanesulfonate, gentamicin, vancomycin, cisplatin, tacrolimus, and pharmaceutically acceptable salts thereof.

(4) The suppressant according to (1) or (2), in which the megalin ligand is at least one megalin ligand which is selected from the group consisting of colistin, colistin methanesulfonate, and pharmaceutically acceptable salts thereof.

(5) Cilastatin or a pharmaceutically acceptable salt thereof for use in suppressing renal impairment or inner ear disorders induced via megalin by at least one megalin ligand which is selected from the group consisting of polymyxins, aminoglycoside antibiotics, glycopeptide antibiotics, cisplatin, tacrolimus, and pharmaceutically acceptable salts thereof.

(6) The cilastatin or pharmaceutically acceptable salt thereof according to (5) for use in suppressing inner ear disorders.

(7) A formulation which combines cilastatin or a pharmaceutically acceptable salt thereof with at least one active component which is selected from the group consisting of colistin, colistin methanesulfonate, and pharmaceutically acceptable salts thereof, wherein the combined formulation is for use simultaneously, separately, or at time intervals.

(8) A pharmaceutical composition including cilastatin or a pharmaceutically acceptable salt thereof, at least one active component which is selected from the group consisting of colistin, colistin methanesulfonate, and pharmaceutically acceptable salts thereof, and a pharmaceutically acceptable carrier.

(9) An anti-microbial agent including cilastatin or a pharmaceutically acceptable salt thereof, at least one active component which is selected from the group consisting of colistin, colistin methanesulfonate, and pharmaceutically acceptable salts thereof, and a pharmaceutically acceptable carrier.

(10) The anti-microbial agent according to (9) which includes 0.5 parts by mass to 200 parts by mass of cilastatin or a pharmaceutically acceptable salt thereof with respect to 1 part by mass of colistin, colistin methanesulfonate, or a pharmaceutically acceptable salt thereof.

(11) The anti-microbial agent according to (9) which includes 1.5 parts by mass to 3 parts by mass of cilastatin or a pharmaceutically acceptable salt thereof with respect to 1 part by mass of colistin, colistin methanesulfonate, or a pharmaceutically acceptable salt thereof.

(12) Use of cilastatin or a pharmaceutically acceptable salt thereof for producing a suppressant for renal impairment or inner ear disorders induced via megalin by at least one megalin ligand which is selected from the group consisting of polymyxins, aminoglycoside antibiotics, glycopeptide antibiotics, cisplatin, tacrolimus, and pharmaceutically acceptable salts thereof.

(13) The use according to (12) for producing a suppressant for inner ear disorders.

(14) The use according to (12) or (13), in which the megalin ligand is at least one megalin ligand which is selected from the group consisting of colistin, colistin methanesulfonate, gentamicin, vancomycin, cisplatin, tacrolimus, and pharmaceutically acceptable salts thereof.

(15) The use according to (12) or (13), wherein the megalin ligand is at least one megalin ligand which is selected from the group consisting of colistin, colistin methanesulfonate, and pharmaceutically acceptable salts thereof.

(16) A pharmaceutical kit including cilastatin or a pharmaceutically acceptable salt thereof in a first compartment, and at least one megalin ligand which is selected from the group consisting of colistin, colistin methanesulfonate, and pharmaceutically acceptable salts thereof in a second compartment.

(17) A megalin antagonist including cilastatin or a pharmaceutically acceptable salt thereof as an active component.

(18) The megalin antagonist according to (17), which is for use in suppressing cell damage caused by a megalin ligand being excessively taken into a cell.

(19) The megalin antagonist according to (17), which is for use in suppressing renal impairment or inner ear disorders.

(20) The megalin antagonist according to (17), which is for use in suppressing inner ear disorders.

(21) The megalin antagonist according to (17), wherein the megalin ligand is at least one megalin ligand which is selected from the group consisting of colistin, colistin methanesulfonate, and pharmaceutically acceptable salts thereof.

Advantageous Effects of Invention

Cilastatin or a pharmaceutically acceptable salt thereof, a megalin antagonist including cilastatin or a pharmaceutically acceptable salt thereof as an active component (may be referred to below as the "antagonist according to the present invention"), a suppressant for renal impairment or inner ear disorders caused by megalin ligands, the suppressant including cilastatin or a pharmaceutically acceptable salt thereof as an active component (may be referred to below as the "suppressant according to the present invention"), and a pharmaceutical composition including cilastatin or a pharmaceutically acceptable salt thereof as an active component (may be referred to below as the "pharmaceutical composition according to the present invention") according to the present invention can be taken comparatively safely, and it is possible to inhibit the uptake of various types of megalin ligands which cause severe cell damage into cells via megalin. For this reason, cilastatin or a pharmaceutically acceptable salt thereof, the megalin antagonists, the suppressant, and the pharmaceutical composition can be used in order to inhibit cell damage induced via megalin by the megalin ligands or diseases derived therefrom, for example, renal impairment or inner ear disorders (that is, use is possible as a prophylactic or therapeutic agent for these disease) while maintaining the primary efficacy of the various types of megalin ligands. In addition, it is possible to provide a therapy combining cilastatin or a pharmaceutically acceptable salt thereof with a megalin ligand.

It should be noted that, in the present invention, "suppressing cell damage induced by various types of megalin ligands or diseases derived therefrom" refers to completely eliminating the expression of cell damage or the symptoms of diseases derived therefrom caused by the uptake of the megalin ligands into the cells, for example, renal impairment or inner ear disorders, alleviating the symptoms in comparison with a time when only the megalin ligand is used, or alleviating the symptoms already expressed, and "alleviating" includes reducing the extent of the symptoms or completely eliminating the symptoms. In the present specification, completely preventing the expression of symptoms of the diseases or alleviating the symptoms compared to a time when only the megalin ligand is used is referred to as "prevention" while alleviating the symptoms already expressed is referred to as "treatment", and a pharmaceutical provided for the "prevention" or the "treatment" may be referred to as a "prophylactic agent" or a "therapeutic agent", respectively. In addition, a pharmaceutical for "suppressing disease" may be referred to as a "suppressant".

In addition, in the present specification, the "megalin antagonist" is also referred to as a "megalin ligand antagonist" or a "megalin ligand receptor antagonist".

DESCRIPTION OF EMBODIMENTS

Figure 1A:
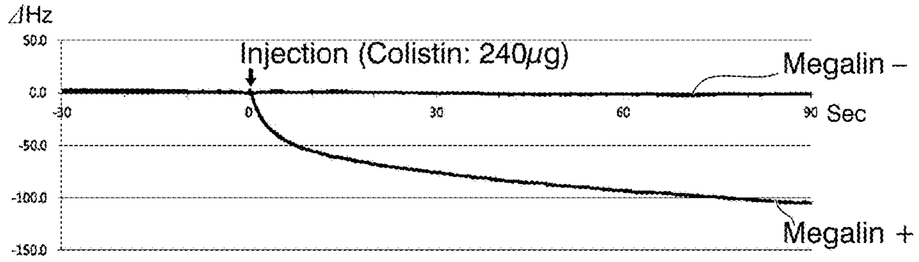
FIG. 1A is a diagram which shows changes in frequency over time in a case of adding colistin to a chip where megalin is immobilized using the QCM method in Reference Example 1.
Figure 1B:
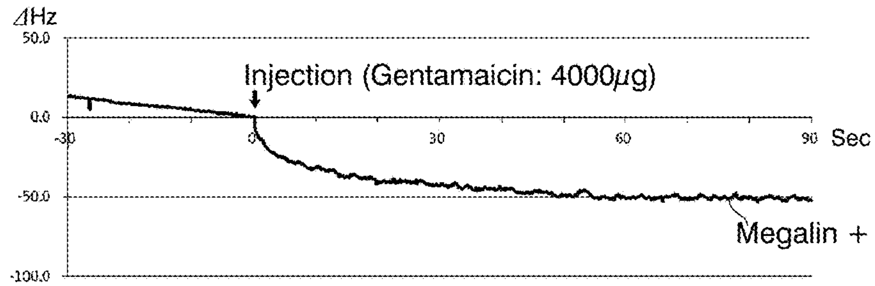
FIG. 1B is a diagram which shows changes in frequency over time in a case of adding gentamicin to a chip where megalin is immobilized using the QCM method in Reference Example 1.
Figure 1C:
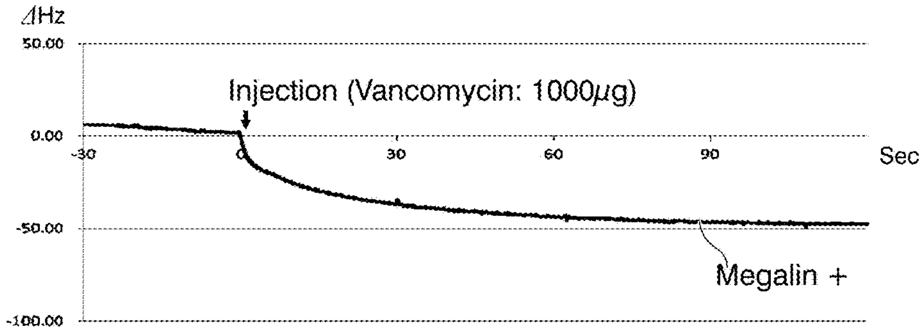
FIG. 1C is a diagram which shows changes in frequency over time in a case of adding vancomycin to a chip where megalin is immobilized using the QCM method in Reference Example 1.
Figure 1D:
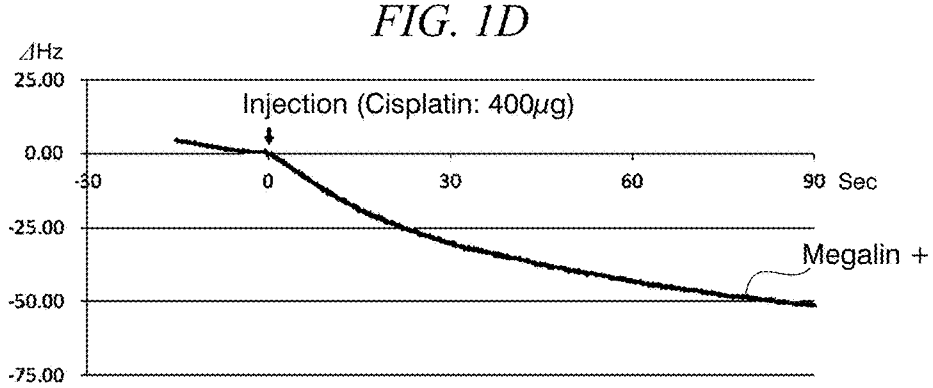
FIG. 1D is a diagram which shows changes in frequency over time in a case of adding cisplatin to a chip where megalin is immobilized using the QCM method in Reference Example 1.
Figure 1E:
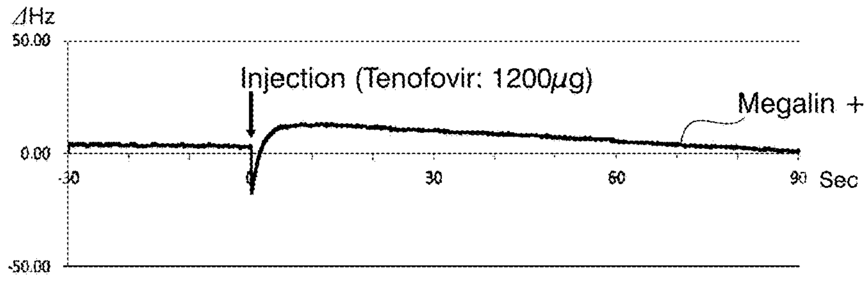
FIG. 1E is a diagram which shows changes in frequency over time in a case of adding tenofovir to a chip where megalin is immobilized using the QCM method in Reference Example 1.
Figure 1F:
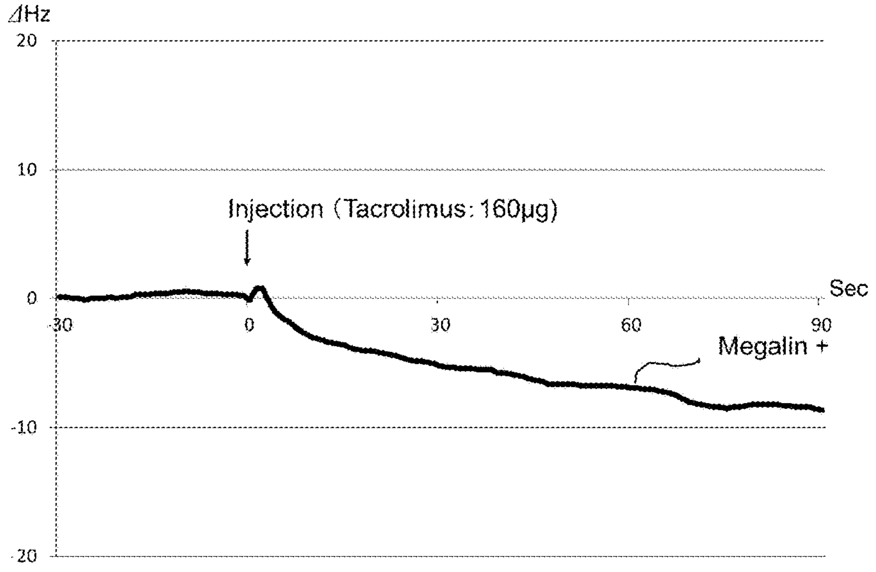
FIG. 1F is a diagram which shows changes in frequency over time in a case of adding tacrolimus to a chip where megalin is immobilized using the QCM method in Reference Example 1.

In the cilastatin or pharmaceutically acceptable salt thereof according to the present invention (also referred to as a "pharmacologically acceptable salt" in the present specification), examples of the pharmaceutically acceptable salt include alkali metal salts such as sodium salt and potassium salt; alkaline earth metal salts such as magnesium salts and calcium salts; aluminum salt; amine salts such as trimethylamine salt, triethylamine salt, dicyclohexylamine salt, dibenzylamine salt, phenethyl benzyl amine salt, procaine salt, morpholine salt, pyridine salt, piperidine salt, and N-ethylpiperidine salt; ammonium salt; basic amino acid salts such as lysine salt and arginine salt; and the like. Among these, cilastatin sodium is particularly preferable.

As the cilastatin or a pharmaceutically acceptable salt thereof, for example, it is possible to use a commercially available product, or to produce or obtain the cilastatin or a pharmaceutically acceptable salt using a known method or a method based on a known method.

As one aspect of the present invention, the cilastatin or pharmaceutically acceptable salt thereof is not used in combination with imipenem. That is, as one aspect of the present invention, the suppressant according to the present invention, the pharmaceutical composition according to the present invention, and the antagonist according to the present invention do not include imipenem, and, in the treatment method or prevention method according to the present invention, imipenem is not administered simultaneously or separately.

Cilastatin binds to the extracellular region of megalin. For this reason, cilastatin or pharmaceutically acceptable salts thereof compete with megalin ligands and, as a result, are able to suppress the binding of megalin ligands to megalin and to suppress the uptake of megalin ligands into the cells. For this reason, the cilastatin or a pharmaceutically acceptable salt thereof according to the present invention is preferably used in order to suppress cell damage caused by megalin ligands being excessively taken into the cells. That is, one aspect of the present invention is a megalin antagonist in which cilastatin or a pharmaceutically acceptable salt thereof is an active component.

Since megalin is expressed in kidney proximal tubule epithelial cells (primarily, the luminal membrane), inner ear epithelial cells, the testes, and the neural ectoderm, the cilastatin or a pharmaceutically acceptable salt thereof according to the present invention, the suppressant according to the present invention, the pharmaceutical composition according to the present invention, and the antagonist according to the present invention are effective for suppressing (that is, as a prophylactic agent or a therapeutic agent) cell damage with respect to these cells which is induced via megalin by various types of megalin ligands, and diseases derived therefrom.

An aspect of the present invention is the use of the cilastatin or a pharmaceutically acceptable salt thereof according to the present invention, the suppressant according to the present invention, the pharmaceutical composition according to the present invention, or the antagonist according to the present invention for the suppression (that is, prevention or treatment) of renal impairment while maintaining the main efficacy of various types of megalin ligands.

Another aspect of the present invention is the use of the cilastatin or a pharmaceutically acceptable salt thereof according to the present invention, the suppressant according to the present invention, the pharmaceutical composition according to the present invention, or the antagonist according to the present invention for the suppression (that is, prevention or treatment) of drug-induced renal impairment or diabetic nephropathy while maintaining the main efficacy of various types of megalin ligands.

Still another aspect of the present invention is the use of the cilastatin or a pharmaceutically acceptable salt thereof according to the present invention, the suppressant according to the present invention, the pharmaceutical composition according to the present invention, or the antagonist according to the present invention for the suppression (that is, prevention or treatment) of diseases or symptoms other than drug-induced renal impairment while maintaining the main efficacy of various types of megalin ligands.

Still another aspect of the present invention is the use of the cilastatin or a pharmaceutically acceptable salt thereof according to the present invention, the suppressant according to the present invention, the pharmaceutical composition according to the present invention, or the antagonist according to the present invention for the suppression (that is, prevention or treatment) of inner ear disorders, for example, tinnitus, dizziness, or hearing loss, while maintaining the main efficacy of various types of megalin ligands.

The megalin ligands of which the binding to megalin is inhibited by the cilastatin or a pharmaceutically acceptable salt thereof according to the present invention, the suppressant according to the present invention, the pharmaceutical composition according to the present invention, or the antagonist according to the present invention are not particularly limited as long as the megalin ligands are a substance having the ability to bind to megalin. For example, the cilastatin or a pharmaceutically acceptable salt thereof according to the present invention, the suppressant according to the present invention, the pharmaceutical composition according to the present invention, or the antagonist according to the present invention can be used as a compound, suppressant, pharmaceutical composition, or antagonist having an antagonistic action with respect to the megalin binding ability of each of the substances illustrated above in the description in NPL 3.

The cilastatin or a pharmaceutically acceptable salt thereof according to the present invention, the suppressant according to the present invention, the pharmaceutical composition according to the present invention, or the antagonist according to the present invention are preferably used as a compound, suppressant, pharmaceutical composition, or antagonist having an antagonistic action with respect to the megalin binding ability of the megalin ligands which can be causes leading to cell damage via megalin. By using the compound according to the present invention, the suppressant according to the present invention, the pharmaceutical composition according to the present invention, or the antagonist according to the present invention, a cell protection effect is obtained which can attenuate the influence of causes leading to cell damage which have a binding ability to megalin (that is, megalin ligands which can be causes leading to cell damage via megalin). Examples of megalin ligands which can be causes leading to cell damage via megalin include substances having a megalin binding ability among anti-microbial agents, anti-viral agents, immunosuppressive agents, anti-cancer drugs, and the like, or biological factors such as albumin. The compound according to the present invention, the suppressant according to the present invention, the pharmaceutical composition according to the present invention, or the antagonist according to the present invention has an antagonistic action on the megalin binding ability of at least one megalin ligand which is selected from the group consisting of polymyxins such as colistin (also referred to as polymyxin E) and colistin methanesulfonate; aminoglycoside antibiotics such as gentamicin; glycopeptide antibiotics such as vancomycin; cisplatin; and tacrolimus; and pharmaceutically acceptable salts thereof, and is preferably used to suppress cell damage induced via megalin by megalin ligands, or diseases derived therefrom, for example, renal impairment or inner ear disorders, while maintaining the main efficacy of the megalin ligand, among these, the above preferably have an antagonistic action with respect to the megalin binding ability of at least one megalin ligand which is selected from the group consisting of colistin, colistin methanesulfonate, gentamicin, vancomycin, cisplatin, tacrolimus, and pharmaceutically acceptable salts thereof, in particular, colistin, colistin methanesulfonate, pharmaceutically acceptable salts thereof, and are preferably used in order to suppress cell damage induced via megalin by the above or diseases derived therefrom, for example, renal impairment or inner ear disorders while maintaining the main efficacy of the megalin ligand.

In the present specification, colistin normally refers to a mixture of colistin A (N-[3-amino-1 [[1-[[3-amino-1-[[6,9,18-tris (2-aminoethyl)-3-(1-hydroxyethyl)-12,15-bis (2-methylpropyl)-2,5,8,11,14,17,20-heptaoxo-1,4,7,10,13,16,19-heptazacyclotricos-21-yl]carbamoyl] propyl] carbamoyl]-2-hydroxypropyl] carbamoyl] propyl]-6-methyl-octanamide), and colistin B (N-[3-amino-1[[1-[[3-amino-1-[[6,9,18-tris (2-aminoethyl)-3-(1-hydroxyethyl)-12,15-bis (2-methylpropyl)-2,5,8,11,14,17,20-heptaoxo-1,4,7,10,13,16,19-heptazacyclotricos-21-yl] carbamoyl] propyl] carbamoyl]-2-hydroxypropyl] carbamoyl] propyl]-5-methylheptanamide), but may include only one of colistin A or colistin B.

In addition, in the present specification, colistin methanesulfonate refers to a compound in which some or all of the five amino groups in one molecule of the colistin ($—NH_2$), more preferably all, have been sulfomethylated.

"Pharmaceutically acceptable salts" of the megalin ligand refer to conventional salts used in the field of medicine and examples thereof include base addition salts or an amino group in the carboxyl group in the case of having a carboxyl group, the amino group in the case of having an imino group or a basic heterocyclic group, or salts of acid addition salts in an imino group or a basic heterocyclic group.

Examples of base addition salts include alkali metal salts such as sodium salt and potassium salt; alkaline earth metal salts such as calcium salt and magnesium salt; for example, ammonium salts; organic amine salts such as trimethylamine salt, triethylamine salt, dicyclohexylamine salt, ethanolamine salt, diethanolamine salt, triethanolamine salt, procaine salt, and N,N'-dibenzylethylenediamine salts.

Examples of acid addition salts include inorganic acid salts such as hydrochloric acid salt, sulfate salt, nitrate salt, phosphate salt, and perchlorate salt; organic acid salts such as maleate salt, fumaric acid salt, tartrate salt, citrate salt, ascorbate salt, and trifluoroacetic acid salt; sulfonic acid salts such as methane sulfonate, isethionate, benzene sulfonate, and p-toluene sulfonic acid salts; and the like.

Sulfate salt is preferable as the pharmaceutically acceptable salt of colistin and sodium salt is preferable as the pharmaceutically acceptable salt of colistin methanesulfonate.

Examples of main efficacies of colistin, colistin methanesulfonate, and pharmaceutically acceptable salts thereof include known anti-microbial effects and the above can be used in the treatment or prevention of various infectious diseases caused by *Pseudomonas aeruginosa, Acinetobacter* spp., *E. coli, Citrobacter* spp., *Enterobacter* spp., *Klebsiella* spp., and the like. In particular, it is considered that the above have an efficacy with respect to multidrug-resistant Gram-negative bacteria infections such as multidrug-resistant *Pseudomonas aeruginosa*, multidrug-resistant *Acinetobacter* spp., and multidrug-resistant *Klebsiella* spp.

As the megalin ligand or the pharmaceutically acceptable salts thereof, it is possible to use a commercially available product, or to produce or obtain the megalin ligand or the pharmaceutically acceptable salts thereof using a known method or a method based on a known method.

The cilastatin or pharmaceutically acceptable salt thereof according to the present invention can be formulated into solid agents such as powders, granules, capsules, tablets, and chewable tablets, solutions or liquid drugs such as syrups, injectable solutions, sprays, or the like by conventional methods, and can be used as the antagonist according to the present invention, the suppressant according to the present invention, or the pharmaceutical composition according to the present invention. As the antagonist according to the present invention, the suppressant according to the present invention, or the pharmaceutical composition according to the present invention, an injectable solution is preferable.

The antagonist according to the present invention, the suppressant according to the present invention, or the pharmaceutical composition according to the present invention is formulated by blending, as necessary in the formulation, a suitable pharmaceutically acceptable carrier, for example, an excipient, a binder, a lubricant, a solvent, a disintegrating agent, a solubilizing agent, a suspending agent, an emulsifier, an isotonic agent, a stabilizer, a soothing agent, a preservative, an antioxidant, a flavoring agent, a coloring agent, and the like with cilastatin or a pharmaceutically acceptable salt thereof, which is the active component (may be referred to below as cilastatin or the like).

Examples of excipients include saccharides such as lactose, glucose, and D-mannitol; starches; organic excipients such as cellulose such as crystalline cellulose; inorganic excipients such as dicalcium phosphate, calcium carbonate, kaolin, and the like. Examples of binders include α-starch, gelatin, gum arabic, methylcellulose, carboxymethyl cellulose, carboxymethyl cellulose sodium, crystalline cellulose, D-mannitol, trehalose, hydroxypropyl cellulose, hydroxypropyl methylcellulose, polyvinylpyrrolidone, polyvinyl alcohol, and the like. Examples of lubricants include fatty acid salts such as stearic acid and stearic acid salt, talc, silicates, and the like. Examples of solvents include purified water, physiological saline, and the like. Examples of disintegrating agents include low-substituted hydroxypropyl cellulose, chemically modified cellulose and starches, alginic acid, and the like. Examples of solubilizing agents include polyethylene glycol, propylene glycol, trehalose, benzyl benzoate, ethanol, sodium carbonate, sodium citrate, sodium salicylate, sodium acetate, and the like. Examples of suspending agents or emulsifiers include celluloses such as sodium lauryl sulfate, gum arabic, gelatin, lecithin, glyceryl monostearate, polyvinyl alcohol, polyvinylpyrrolidone, and carboxymethyl cellulose sodium; polysorbates, polyoxyethylene hydrogenated castor oil, and the like. Examples of isotonic agents include sodium chloride, potassium chloride, saccharides, glycerin, urea, and the like. Examples of stabilizers include polyethylene glycol, sodium dextran sulfate, other amino acids, and the like. Examples of soothing agents include glucose, calcium gluconate, procaine hydrochloride, and the like. Examples of preservatives include paraoxybenzoate esters, chlorobutanol, benzyl alcohol, phenethyl alcohol, dehydroacetic acid, sorbic acid, and the like. Examples of antioxidants include sulfite, ascorbic acid, and the like. Examples of flavoring agents include sweeteners, flavorings, and the like normally used in the pharmaceutical and food sectors. Examples of coloring agents include coloring materials normally used in the pharmaceutical and food sectors.

The pharmaceutical composition according to the present invention may further contain other active components. As the other active components, a megalin ligand of which the megalin-mediated uptake into cells is inhibited by the cilastatin or a pharmaceutically acceptable salt thereof according to the present invention is preferable; more specifically, at least one megalin ligand which is selected from the group consisting of polymyxins such as colistin and colistin methanesulfonate; aminoglycoside antibiotics such as gentamicin; glycopeptide antibiotics such as vancomycin; cisplatin; and tacrolimus; and pharmaceutically acceptable salts thereof is preferable; among these, at least one megalin ligand which is selected from the group consisting of colistin, colistin methanesulfonate, gentamicin, vancomycin, cisplatin, and tacrolimus, and pharmaceutically acceptable salts thereof is more preferable, in particular, colistin, colistin methanesulfonate, and pharmaceutically acceptable salts thereof are preferable.

One aspect of the present invention is a pharmaceutical composition including cilastatin or a pharmaceutically acceptable salt thereof, at least one megalin ligand which is selected from the group consisting of polymyxins, aminoglycoside antibiotics, glycopeptide antibiotics, cisplatin, tacrolimus, and pharmaceutically acceptable salts thereof, and a pharmaceutically acceptable carrier, and the pharmaceutical composition preferably does not include imipenem.

Another aspect of the present invention is a pharmaceutical composition including cilastatin or a pharmaceutically acceptable salt thereof, at least one active component which is selected from the group consisting of colistin, colistin methanesulfonate, gentamicin, vancomycin, cisplatin, tacrolimus, and pharmaceutically acceptable salts thereof, and a pharmaceutically acceptable carrier, and the pharmaceutical composition preferably does not include imipenem.

Another aspect of the present invention is a pharmaceutical composition including cilastatin or a pharmaceutically acceptable salt thereof, at least one active component which is selected from the group consisting of colistin, colistin methanesulfonate, and pharmaceutically acceptable salts thereof, and a pharmaceutically acceptable carrier, and the pharmaceutical composition preferably does not include imipenem.

Another aspect of the present invention is an anti-microbial agent (also referred to as an anti-microbial composition) including cilastatin or a pharmaceutically acceptable salt thereof, at least one active component which is selected from the group consisting of colistin, colistin methanesulfonate, and pharmaceutically acceptable salts thereof, and a pharmaceutically acceptable carrier, and the anti-microbial agent preferably does not include imipenem. In addition, the anti-microbial agent is preferably an anti-microbial agent having anti-microbial activity against *Pseudomonas aeruginosa, Acinetobacter* spp., *E. coli, Citrobacter* spp., *Enterobacter* spp., *Klebsiella* spp., and the like, and more preferably an anti-microbial agent having an anti-microbial activity against multidrug-resistant Gram-negative bacilli such as multidrug-resistant *Pseudomonas aeruginosa*, multidrug-resistant *Acinetobacter* spp, and multidrug-resistant *Klebsiella* spp.

In the pharmaceutical composition according to the present invention, in a case where the pharmaceutical composition includes the megalin ligand, it is sufficient if the blending amount of the megalin ligands is a therapeutically effective amount for the main efficacy with respect to the target to which the administration of the megalin ligand is necessary.

In the pharmaceutical compositions according to the present invention, the blending amount of the cilastatin or a pharmaceutically acceptable salt thereof and the megalin ligand is preferably 0.5:1 to 200:1, more preferably 0.5:1 to 100:1, and even more preferably 0.5:1 to 40:1, by mass ratio represented by (the mass of the cilastatin or a pharmaceutically acceptable salt thereof):(the mass of the megalin ligand).

The cilastatin or a pharmaceutically acceptable salt thereof has no anti-microbial activity, in addition, even when using a combination of the cilastatin or a pharmaceutically acceptable salt thereof and colistin, colistin methanesulfonate, or pharmaceutically acceptable salts thereof, there is no influence on the anti-microbial activity of colistin, colistin methanesulfonate, or pharmaceutically acceptable salts thereof. Accordingly, it is possible to blend an effective amount of the cilastatin or pharmaceutically acceptable salt thereof in the pharmaceutical composition according to the present invention in order to suppress, for example, renal impairment or inner ear disorders caused by colistin, colistin methanesulfonate, or pharmaceutically acceptable salts thereof. More specifically, with respect to 1 part by mass of colistin, colistin methanesulfonate, or pharmaceutically acceptable salts thereof the cilastatin or pharmaceutically acceptable salt thereof is preferably 0.5 parts by mass to 200 parts by mass, more preferably 0.5 parts by mass to 100 parts by mass, more preferably 0.5 parts by mass to 40 parts by mass, more preferably 1.5 parts by mass to 10 parts by mass, more preferably 1.5 parts by mass to 7 parts by mass, even more preferably 1.5 parts by mass to 4 parts by mass, and particularly preferably 1.5 parts by mass to 3 parts by mass, or 3 parts by mass to 4 parts by mass.

According to the present invention, in a case where the inhibitor, the antagonist, or the pharmaceutical composition is an injectable agent, the form of the injectable agent may be a form in which cilastatin or a pharmaceutically acceptable salt thereof, which is an active component, a suitable pharmaceutically acceptable carrier, and other components as desired in the case of a pharmaceutical composition are dissolved in advance, or may be a form in which the components are dissolved at the time of use as is in a powder or after being added to a suitable carrier (an additive). These injectable solutions preferably include, for example, 0.1 mass % to 1 mass % of cilastatin or a pharmaceutically acceptable salt thereof as an active component based on the mass of the total formulation. Examples of suitable solvents or diluents in the case of an injectable solution include distilled water for injection, a lidocaine hydrochloride solution (for intramuscular injection), saline, a glucose aqueous solution, ethanol, polyethylene glycol, propylene glycol, liquid for intravenous injection (for example, an aqueous solution of citric acid and sodium citrate) or an electrolyte solution (for intravenous drip infusion and intravenous injection), and the like, or a mixed solution thereof.

One aspect of the present invention is a method for suppressing (that is, a treatment method or prevention method) drug-induced renal impairment, diabetic nephropathy, or inner ear disorders (tinnitus, dizziness, hearing loss, or the like) induced via megalin by a variety of megalin ligands, the method including administering to a subject in need thereof a therapeutically effective amount of cilastatin or a pharmaceutically acceptable salt thereof, or the suppressant according to the present invention, the pharmaceutical composition according to the present invention, or the antagonist according to the present invention, which include a therapeutically effective amount of cilastatin or a pharmaceutically acceptable salt thereof.

Another aspect of the present invention is a method for suppressing (that is, a treatment method or prevention method) drug-induced renal impairment, or inner ear disorders (tinnitus, dizziness, hearing loss, or the like) induced via megalin by the megalin ligands, the method including administering to a subject in need thereof a therapeutically effective amount of cilastatin or a pharmaceutically acceptable salt thereof, or the suppressant according to the present invention, the pharmaceutical composition according to the present invention, or the antagonist according to the present invention, which include a therapeutically effective amount of cilastatin or a pharmaceutically acceptable salt thereof, in combination with at least one megalin ligand which is selected from the group consisting of a therapeutically effective amount of polymyxins, aminoglycoside antibiotics, glycopeptide antibiotics, cisplatin, tacrolimus, and pharmaceutically acceptable salts thereof.

Another aspect of the present invention is a method for suppressing (that is, a treatment method or prevention method) drug-induced renal impairment, or inner ear disorders (tinnitus, dizziness, hearing loss, or the like) induced via megalin by the megalin ligands, the method including administering to a subject in need thereof a therapeutically effective amount of cilastatin or a pharmaceutically acceptable salt thereof, or the suppressant according to the present invention, the pharmaceutical composition according to the present invention, or the antagonist according to the present invention, which include a therapeutically effective amount of cilastatin or a pharmaceutically acceptable salt thereof, in combination with at least one megalin ligand which is selected from the group consisting of a therapeutically effective amount of colistin, colistin methanesulfonate, gentamicin, vancomycin, cisplatin, tacrolimus, and pharmaceutically acceptable salts thereof.

Another aspect of the present invention is a method for suppressing (that is, a treatment method or prevention method) drug-induced renal impairment, or inner ear disorders (tinnitus, dizziness, hearing loss, or the like) induced via megalin by colistin, colistin methanesulfonate, and pharmaceutically acceptable salts thereof, the method including administering a therapeutically effective amount of cilastatin or a pharmaceutically acceptable salt thereof, or the suppressant according to the present invention, the pharmaceutical composition according to the present invention, or the antagonist according to the present invention, which include a therapeutically effective amount of cilastatin or a pharmaceutically acceptable salt thereof, in combination with a therapeutically effective amount of colistin, colistin methanesulfonate, or pharmaceutically acceptable salts thereof.

Yet another aspect of the present invention is a method for treating or a method for preventing infections including administering to a subject in need thereof a therapeutically effective amount of cilastatin or a pharmaceutically acceptable salt thereof, or the suppressant according to the present invention, the pharmaceutical composition according to the present invention, or the antagonist according to the present invention, which include a therapeutically effective amount of cilastatin or a pharmaceutically acceptable salt thereof, in combination with a therapeutically effective amount of colistin, colistin methanesulfonate, or pharmaceutically acceptable salts thereof.

In the present specification, "a target to which administration is necessary" refers to a target having symptoms of drug-induced renal impairment, diabetic nephropathy, or inner ear disorders induced via megalin by various types of megalin ligands, or at risk of having such symptoms.

As the cilastatin or a pharmaceutically acceptable salt thereof according to the present invention, the suppressant according to the present invention, the pharmaceutical composition according to the present invention, or the antagonist according to the present invention, cilastatin or a pharmaceutically acceptable salt thereof a suppressant, a pharmaceutical composition, or an antagonist administered to an animal to which administration is necessary is preferable; cilastatin or a pharmaceutically acceptable salt thereof, a suppressant, a pharmaceutical composition, or an antagonist administered to a mammal to which administration is necessary is more preferable; cilastatin or a pharmaceutically acceptable salt thereof, a suppressant, a pharmaceutical composition, or an antagonist administered to a human to which administration is necessary, to a domestic animal such as a mouse, rat, rabbit, guinea pig, hamster, monkey, sheep, horse, cow, pig, donkey, dog, or cat to which administration is necessary, or to a laboratory animal to which administration is necessary is even more preferable; and cilastatin or a pharmaceutically acceptable salt thereof, a suppressant, a pharmaceutical composition, or an antagonist administered to the human is particularly preferable.

The cilastatin or a pharmaceutically acceptable salt thereof according to the present invention, the suppressant according to the present invention, the pharmaceutical composition according to the present invention, or the antagonist according to the present invention may be administered alone to the animal, or may be administered in combination with a megalin ligand (may also be referred to as "co-administration" in the present specification). For example, by co-administration of the megalin ligands which can be a cause leading to cell damage with the cilastatin or a pharmaceutically acceptable salt thereof according to the present invention, the suppressant according to the present invention, the pharmaceutical composition according to the present invention, or the antagonist according to the present invention to an animal, it is possible to effectively suppress cell damage due to the megalin ligands, for example, to suppress renal impairment or inner ear disorders.

It is sufficient if the dose of the cilastatin or a pharmaceutically acceptable salt thereof according to the present invention, the suppressant according to the present invention, the pharmaceutical composition according to the present invention, or the antagonist according to the present invention is an amount sufficient in order to inhibit the binding of the megalin ligands to megalin and the subsequent uptake into the cells, and the dose will be different depending on the species, sex, age, body weight, and diet of the administration target, the mode of administration, the type of the megalin ligand, the symptoms of cell damage caused by the dose, the blending amount and the megalin ligand, the degree of risk that cell damage will be induced, and the like. For example, the daily dose of the active component for an adult (body weight 60 kg) is preferably 0.5 g to 2.0 g for cilastatin, more preferably 0.5 g to 1.5 g, even more preferably 0.5 g to 1.0 g, and particularly preferably 0.5 g to 0.8 g. It is possible to administer such doses once or several times, more preferably over two to four times. In addition, the use of an administration method such as every other day administration or at intervals of two days is also possible.

The cilastatin or a pharmaceutically acceptable salt thereof according to the present invention, the suppressant according to the present invention, or the antagonist according to the present invention can be used in combination with various types of megalin ligands. In a case where the cilastatin or a pharmaceutically acceptable salt thereof according to the present invention, the suppressant according to the present invention, or the antagonist according to the present invention is used in combination with various types of megalin ligands (in the case of co-administration), the administration of the cilastatin or a pharmaceutically acceptable salt thereof, the suppressant, the pharmaceutical composition, or the antagonist may be any of: at the same time as the administration of the megalin ligand, before or after the administration of the megalin ligand, or both before and after the administration of the megalin ligand.

In the co-administration, the individual components or agents can be administered in separate preparations or as a single preparation.

In the co-administration, the mass ratio of the cilastatin or a pharmaceutically acceptable salt thereof and the dose of the megalin ligands may be the same as the mass ratio of the blending amount of the cilastatin or a pharmaceutically acceptable salt thereof and the megalin ligand in a case where the pharmaceutical composition according to the present invention includes the megalin ligand.

One aspect of the present invention is a formulation which combines the cilastatin or a pharmaceutically acceptable salt thereof according to the present invention, the suppressant according to the present invention, or the antagonist of the present invention with at least one megalin ligand which is selected from the group consisting of polymyxins, aminoglycoside antibiotics, glycopeptide antibiotics, cisplatin, tacrolimus, and pharmaceutically acceptable salts thereof, and the combination formulation is a formulation for use simultaneously, separately, or at time intervals, and a formulation which is for use in suppressing cell damage induced via megalin by the megalin ligands or diseases derived therefrom, for example, renal impairment or inner ear disorders.

Another aspect of the present invention is a formulation which combines the cilastatin or a pharmaceutically acceptable salt thereof according to the present invention, the suppressant according to the present invention, or the antagonist of the present invention with at least one megalin ligand which is selected from the group consisting of colistin, colistin methanesulfonate, gentamicin, vancomycin, cisplatin, tacrolimus, and pharmaceutically acceptable salts thereof, and the combination formulation is a formulation for use simultaneously, separately, or at time intervals, and a formulation which is for use in suppressing cell damage induced via megalin by the megalin ligands or diseases derived therefrom, for example, renal impairment or inner ear disorders.

Another aspect of the present invention is a formulation which combines the cilastatin or a pharmaceutically acceptable salt thereof according to the present invention, the suppressant according to the present invention, or the antagonist of the present invention with at least one effective component which is selected from the group consisting of colistin, colistin methanesulfonate, and pharmaceutically acceptable salts thereof, and the combination formulation is a formulation for use simultaneously, separately, or at time intervals, and a formulation which is for use in suppressing cell damage induced via megalin by the colistin, colistin methanesulfonate, and pharmaceutically acceptable salts thereof or diseases derived therefrom, for example, renal impairment or inner ear disorders.

Yet another aspect of the present invention is a formulation which combines the cilastatin or a pharmaceutically acceptable salt thereof according to the present invention, the suppressant according to the present invention, or the antagonist of the present invention with at least one active component which is selected from the group consisting of colistin, colistin methanesulfonate, or pharmaceutically acceptable salts thereof, and the combination formulation is a formulation for use simultaneously, separately, or at time intervals, and a formulation which is used as an anti-microbial agent, preferably as an anti-microbial agent having anti-microbial activity against *Pseudomonas aeruginosa, Acinetobacter* spp., *E. coli, Citrobacter* spp., *Enterobacter* spp., *Klebsiella* spp., and the like, and more preferably as an anti-microbial agent having anti-microbial activity against multidrug-resistant Gram-negative bacilli such as multidrug-resistant *Pseudomonas aeruginosa*, multidrug-resistant *Acinetobacter* spp., and multidrug-resistant *Klebsiella* spp., that is, a formulation which is used to treat or prevent infections.

The therapeutic unit of the megalin ligand combined with the cilastatin or a pharmaceutically acceptable salt thereof is not particularly limited and can be determined as necessary by a person skilled in the art from the literature of the prior art. Examples thereof are as follows.

In a case where the megalin ligand is colistin, colistin methanesulfonate or a pharmaceutically acceptable salt thereof, the daily dose of the active component for an adult (body weight 60 kg) of the therapeutic unit for colistin, colistin methanesulfonate or a pharmaceutically acceptable salt thereof is preferably 0.05 g to 1.5 g as colistin, more preferably 0.1 g to 1.0 g, and even more preferably 0.15 g to 0.3 g. It is possible to administer such doses once or several times, more preferably over two to four times. In addition, the use of an administration method such as every other day administration or at intervals of two days is also possible.

One aspect of the present invention is a pharmaceutical kit including cilastatin or a pharmaceutically acceptable salt thereof in a first compartment, and at least one megalin ligand which is selected from the group consisting of polymyxins, aminoglycoside antibiotics, glycopeptide antibiotics, cisplatin, tacrolimus, and pharmaceutically acceptable salts thereof in a second compartment.

Another aspect of the present invention is a pharmaceutical kit including cilastatin or a pharmaceutically acceptable salt thereof in a first compartment, and at least one megalin ligand which is selected from the group consisting of colistin, colistin methanesulfonate, gentamicin, vancomycin, cisplatin, tacrolimus, and pharmaceutically acceptable salts thereof in a second compartment.

Another aspect of the present invention is a pharmaceutical kit including cilastatin or a pharmaceutically acceptable salt thereof in a first compartment, and at least one megalin ligand which is selected from the group consisting of colistin, colistin methanesulfonate, and pharmaceutically acceptable salts thereof in a second compartment.

In the pharmaceutical kit, the mass ratio of the cilastatin or a pharmaceutically acceptable salt thereof in the first compartment and the content of the megalin ligand in the second compartment may be the same as the mass ratio of the blending amount of the cilastatin or a pharmaceutically acceptable salt thereof and the megalin ligand in a case where the pharmaceutical composition according to the present invention includes the megalin ligand.

Another aspect of the present invention is a use of cilastatin or a pharmaceutically acceptable salt thereof in order to produce the megalin ligand antagonist.

Another aspect of the present invention is a use of cilastatin or a pharmaceutically acceptable salt thereof in order to produce a suppressant of cell damage induced via megalin by the megalin ligand, or diseases derived therefrom.

Another aspect of the present invention is a use of cilastatin or a pharmaceutically acceptable salt thereof in order to produce a suppressant of drug-induced renal impairment or diabetic nephropathy induced via megalin by the megalin ligand.

Another aspect of the present invention is a use of cilastatin or a pharmaceutically acceptable salt thereof in order to produce a suppressant of diseases or conditions other than drug-induced renal impairment induced via megalin by the megalin ligand.

Yet another aspect of the present invention is a use of cilastatin or a pharmaceutically acceptable salt thereof in order to produce a suppressant of inner ear disorders (for example, tinnitus, dizziness, or hearing loss), induced via megalin by the megalin ligand.

EXAMPLES

Next, detailed description will be given of the present invention through the illustration of examples, and the like; however, the present invention is not limited thereto. In the following Examples and the like, purified megalin from rat kidneys according to the method described in NPL 5 was used as the megalin, cilastatin sodium (produced by Sigma-Aldrich Co. LLC.) was used as the cilastatin, colistin sulfate (produced by Sigma-Aldrich Co. LLC.) was used as the colistin, gentamicin produced by Sigma-Aldrich Co. LLC. was used as the gentamicin, vancomycin produced by Sigma-Aldrich Co. LLC. was used as the vancomycin, tenofovir produced by Sigma-Aldrich Co. LLC. was used as the tenofovir, and cisplatin produced by Bristol-Myers Co., Ltd., was used as the cisplatin.

Reference Example 1

The binding ability of colistin, gentamicin, vancomycin, cisplatin, and tenofovir with respect to megalin was analyzed using the quartz crystal microbalance method (QCM method).

Regarding the immobilization of megalin protein using the Immobilization Kit for AFFINIX (registered trademark) (manufactured by Initium), according to the protocol recommended in the kit, a megalin protein solution adjusted to 12 to 14 μg/mL using Buffer A included in the kit was immobilized by being placed on the crystal installed in the holder.

The crystal where the megalin protein was immobilized was installed in a measurement instrument AFFINIX (registered trademark) (manufactured by Initium) and it was confirmed that the frequency was stabilized, then colistin (240 μg), gentamicin (4000 μg), vancomycin (1600 μg), cisplatin (400 μg), or tenofovir (1200 μg) were injected (all total injection amounts), and the frequency was measured over time. In more detail, 8 μL of each drug solution was injected to the megalin protein-immobilized crystal placed in the surface of water containing 8 mL of buffer, and the frequency was measured. As a control, measurement was also performed in the same manner with respect to a crystal where the megalin protein was not immobilized. The measurement data was analyzed using dedicated analysis software AQUA (produced by Initium).

The measurement results are shown in FIG. 1A to FIG. 1F. As a result, with gentamicin, colistin, vancomycin, cisplatin, and tacrolimus, the frequency was clearly decreased after injection of these compounds and their binding to megalin was confirmed; however, it was not possible to find the binding of tenofovir to megalin.

Colistin, which is a cyclic peptide antibiotic, is currently the only effective drug with respect to multidrug-resistant bacteria and there is a growing need for the use of colistin due to the emergence of infections due to multidrug-resistant bacteria in recent years. However, since colistin has high nephrotoxicity and the pathogenesis thereof is unknown, only limited use is possible and the situation is that insufficient measures are being taken against multidrug-resistant bacteria. The results of this Reference Example make it clear that colistin is a megalin ligand and suggest the possibility that renal impairment due to colistin can be suppressed by a megalin ligand antagonist.

Example 1

The antagonism effect with respect to the binding of colistin to megalin due to cilastatin was investigated using the QCM method.

First, in the same manner as in Reference Example 1, a crystal where a megalin protein was immobilized was installed in a measuring device and it was confirmed that the frequency was stabilized, then 800 μg, 5000 μg, or 10000 μg of cilastatin was injected therein. Next, after it was confirmed that the frequency was stabilized, 240 μg of colistin was injected, the frequency was measured over time, and the measurement data was analyzed in the same manner as for Reference Example 1. As a control, measurement and analysis were carried out in the same manner except that cilastatin was not injected (cilastatin injection amount: 0 μg).

Figure 2:
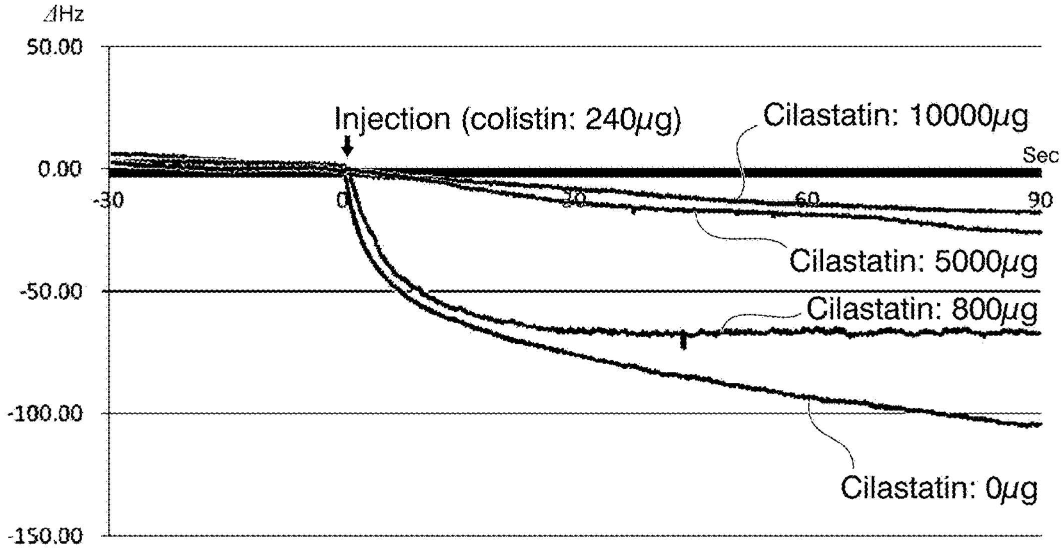
FIG. 2 is a diagram which shows changes in frequency over time in a case of adding colistin after binding cilastatin to a chip where megalin is immobilized using the QCM method in Example 1.

The measurement results are shown in FIG. 2. As a result, it was understood that the greater the cilastatin injection amount, the smaller the frequency changes caused by the colistin injection and that the binding of the colistin to the megalin protein was inhibited depending on the concentration of the cilastatin.

Example 2

The antagonistic action of cilastatin on the binding of gentamicin, vancomycin, cisplatin, and tacrolimus to megalin was investigated using the QCM method.

Specifically, the measurement and analysis of the frequency were carried out in the same manner as for Example 1 except that the injection amount of cilastatin was set to 4000 μg and 4000 μg of gentamicin was used instead of 240 μg of colistin.

In addition, the measurement and analysis of the frequency were carried out in the same manner as for Example 1 except that the injection amount of cilastatin was set to 5000 μg and 1000 μg of vancomycin was used instead of 240 μg of colistin.

In addition, the measurement and analysis of the frequency were carried out in the same manner as for Example 1 except that the injection amount of cilastatin was set to 10000 μg and 800 μg of cisplatin was used instead of 240 μg of colistin.

Furthermore, the measurement and analysis of the frequency were carried out in the same manner as for Example 1 except that the injection amount of cilastatin was set to 2000 μg and 160 μg of tacrolimus was used instead of 240 μg of colistin.

Figure 3:
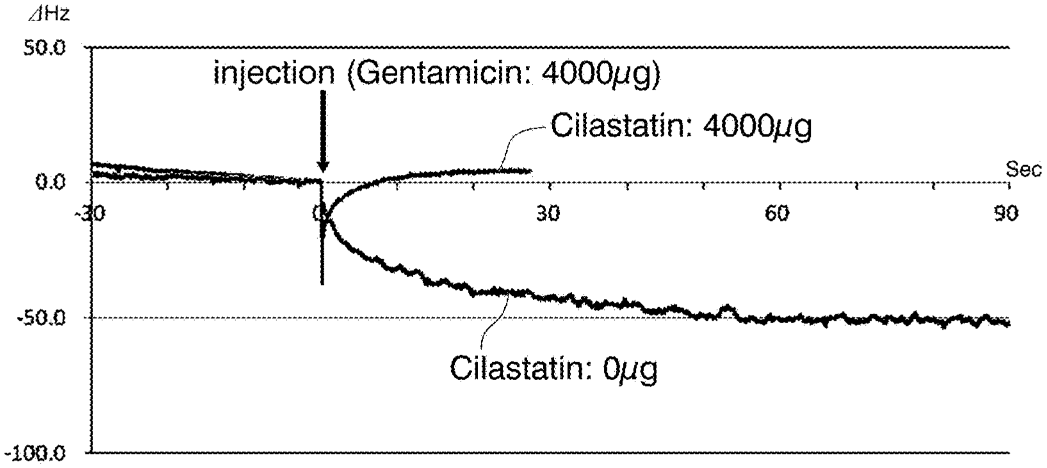
FIG. 3 is a diagram which shows changes in frequency over time in a case of adding gentamicin after binding cilastatin to a chip where megalin is immobilized using the QCM method in Example 2.
Figure 4:
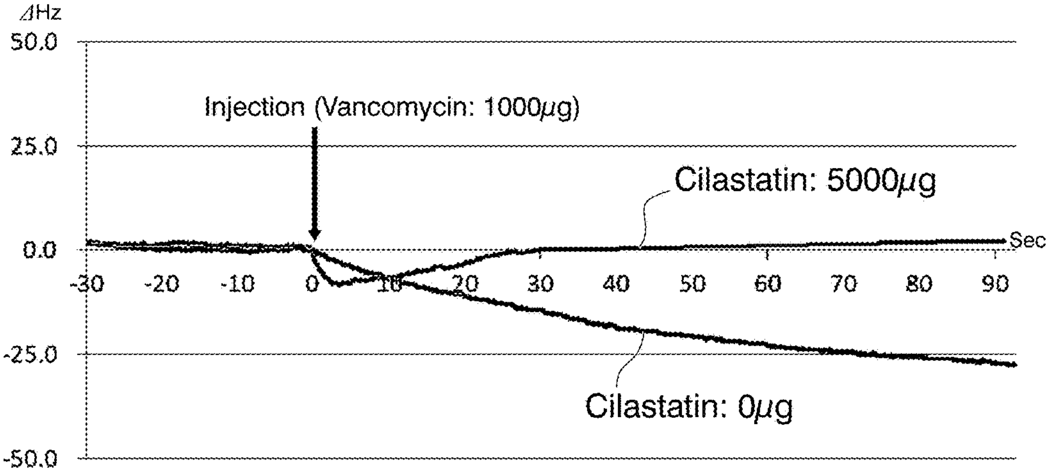
FIG. 4 is a diagram which shows changes in frequency over time in a case of adding vancomycin after binding cilastatin to a chip where megalin is immobilized using the QCM method in Example 2.
Figure 5:
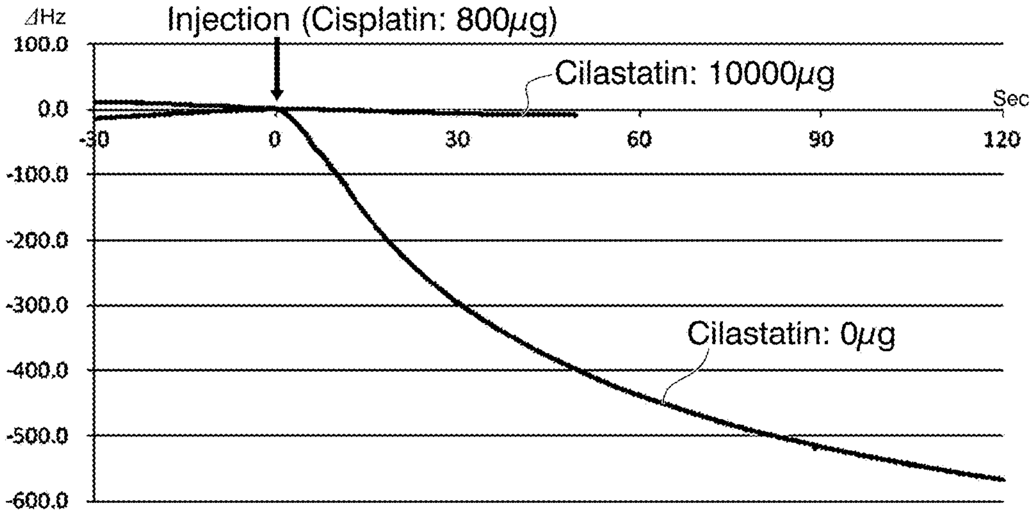
FIG. 5 is a diagram which shows changes in frequency over time in a case of adding cisplatin after binding cilastatin to a chip where megalin is immobilized using the QCM method in Example 2.
Figure 6:
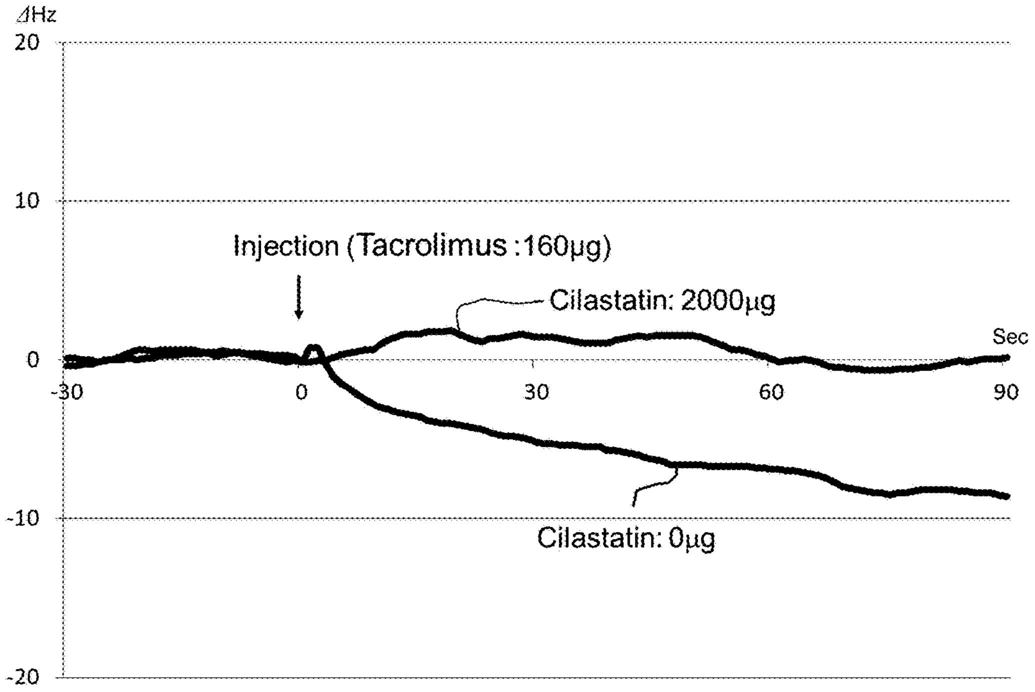
FIG. 6 is a diagram which shows changes in frequency over time in a case of adding tacrolimus after binding cilastatin to a chip where megalin is immobilized using the QCM method in Example 2.

The measurement results in the case of injecting gentamicin are shown in FIG. 3, the measurement results in the case of injecting vancomycin are shown in FIG. 4, the measurement results in the case of injecting cisplatin are shown in FIG. 5, and the measurement results in the case of injecting tacrolimus are shown in FIG. 6. As a result, it was understood that, in a chip bound in advance to cilastatin, the binding of gentamicin, vancomycin, cisplatin, and tacrolimus to megalin protein was inhibited by cilastatin without the frequency being substantially decreased in any of after gentamicin injection, after vancomycin injection, or after cisplatin injection.

Example 3

Cilastatin and colistin were co-administered to rats and it was investigated whether or not nephropathy due to colistin was reduced by the megalin ligand antagonistic action of cilastatin.

In evaluating the colistin nephropathy reduction effect due to cilastatin, a colistin solution and a cilastatin solution were prepared as follows.

In the preparation of the colistin solution, first, a colistin stock solution (colistin concentration: 10 mg/mL) was prepared by dissolving 360 mg of colistin sulfate in 30 mL of a saline solution. The colistin stock solution was sterilized by filtration with a 22 mm PVDF membrane and then stored at 4° C. and a colistin administration solution was prepared by diluting the solution with a saline solution before the colistin administration.

In the preparation of the cilastatin solution, first, a cilastatin sodium solution (cilastatin sodium concentration: 100 mg/mL) was prepared by dissolving 5 g of cilastatin sodium in 50 mL of saline solution. The cilastatin sodium solution was sterilized by filtration with a 22 mm PVDF membrane and then stored at 4° C. until the administration.

The administration and urine collection of each drug solution were carried out as follows. First, 3 days prior to the administration of colistin to Jcl: SD rats (14 weeks of age, male, weight: 450 g to 530 g, from CLEA Japan Inc.), a catheter was placed into the jugular veins. Next, the colistin administration solution prepared as described above was administered as single doses twice daily to the jugular vein over 5 days at intervals of approximately 8 hours and renal impairment was induced. The colistin doses were increased over time as follows: Day 1 (first: 0.5 mg/kg, second: 1.0 mg/kg), Day 2 (first: 1.25 mg/kg, second: 1.25 mg/kg), Day 3 (first: 1.75 mg/kg, second: 2.75 mg/kg), Day 4 (first: 4 mg/kg, second: 4 mg/kg), and Day 5 (4 mg/kg), a total of 20.5 mg/kg was administered over 5 days. Regarding the cilastatin, 100 mg/kg of the cilastatin sodium solution prepared as described above was administered each time as a single dose into the jugular vein before colistin administration. The administration dosage of each administration solution was 1 mL/kg. After the last administration was performed on the morning of Day 5 of administration, spot urine was recovered. Other than the test group in which both of the cilastatin sodium solution and colistin administration solution were administered as described above (cilastatin/colistin administration group (cilastatin/colstin), N=3), as a control, administration and urine collection were carried out in the same manner for a test group in which both of the cilastatin sodium solution and colistin administration solution were replaced with saline (saline/saline-treated group (saline/saline), N=4) and a test group in which only the cilastatin sodium solution was replaced with saline (saline/colistin-administered group (saline/colstin), N=6).

The concentrations of urinary β-D-N-acetyl-glucosaminidase (NAG) and creatinine (CRE) in the recovered urine were each measured using a measurement kit (product name: CREP 2 and BUNK, both were measured by Roche Diagnostics Co., Ltd.) using a discrete method automatic clinical chemistry analyzer (product name: COBAS INTEGRA 400 plus, manufactured by Roche Diagnostics Co., Ltd.), and the urinary NAG/CRE values of each test group were calculated.

Figure 7:
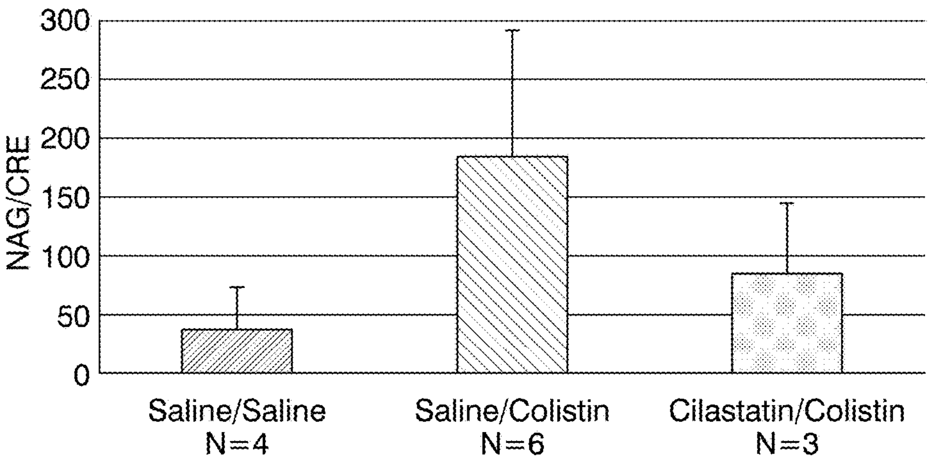
FIG. 7 is a diagram which shows the measurement results of NAG/CRE values in urine 5 days after administration in each test group in Example 3.

The calculation results are shown in FIG. 7. In the group administered with a saline solution and colistin (saline/colistin-administered group), the urinary NAG/CRE values on the fifth day after colistin administration were increased to be 4 times or more those of the non-renal impairment group in which only a saline solution was administered (saline/saline group). The administration group in which the cilastatin and colistin were co-administered (cilastatin/colistin-administered group) exhibited a tendency to have lower values than the saline/colistin-administered group and the colistin-induced renal impairment was reduced by the co-administration of cilastatin.

Reference Example 2

Renal tubular cell damage caused when colistin was administered to megalin mosaic-type knockout mice was analyzed.

Figure 8:
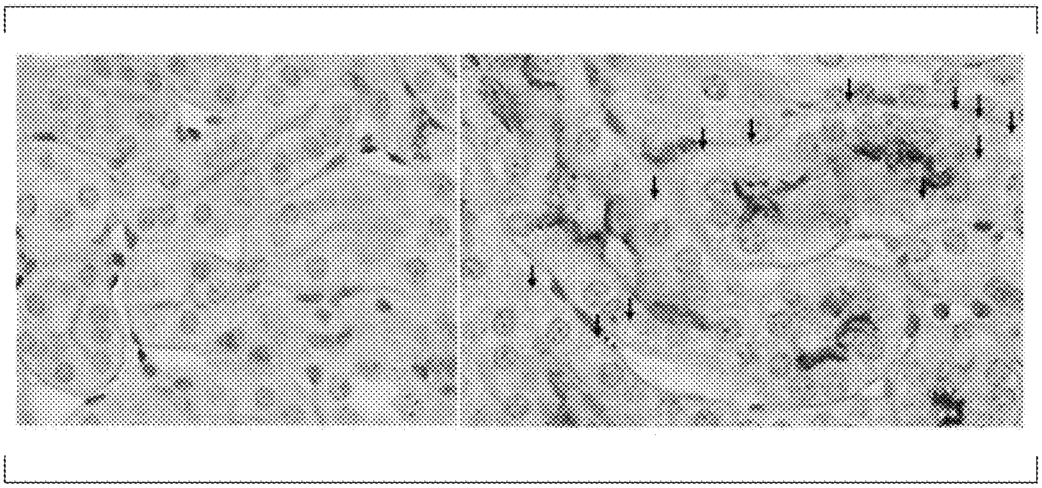
FIG. 8 is a diagram which shows the results (on the left) of immunohistochemical staining of proximal tubular cells in which megalin was expressed in a renal-specific mosaic-type megalin knockout mouse and the results (on the right) of immunohistochemical staining of proximal tubular cells in which the megalin expression was knocked out in Reference Example 2.

First, 12-week-old kidney specific mosaic-type megalin knockout mice (apoE cre/megalin loxP) were used in the experiments (in these mice, genes expressing megalin in about 60% of proximal tubular cells were knocked out). With respect to these mice, the subcutaneous administration of colistin was performed over four days (30 mg/kg/day), after that, proximal tubular cells were analyzed and immunohistochemical staining was performed. The results are shown in FIG. 8.

In the proximal tubular cells expressing megalin (positive megalin immunohistochemical staining) (on the right of FIG. 8), in comparison with the proximal tubular cells in which the expression of megalin was knocked out (negative megalin immunohistochemical staining) (on the left of FIG. 8), numerous vacuoles (arrows) were observed in the cytoplasm.

Reference Example 3

With the same method as in Reference Example 2, colistin was administered to renal-specific mosaic-type megalin knockout mice, after that, the proximal tubular cells were analyzed, and the expression of KIM-1 (Kidney Injury Molecule 1), which is an injury marker of proximal tubular cells, and the expression of megalin were confirmed using a fluorescent double staining method. The results are shown in FIG. 9.

Figure 9:
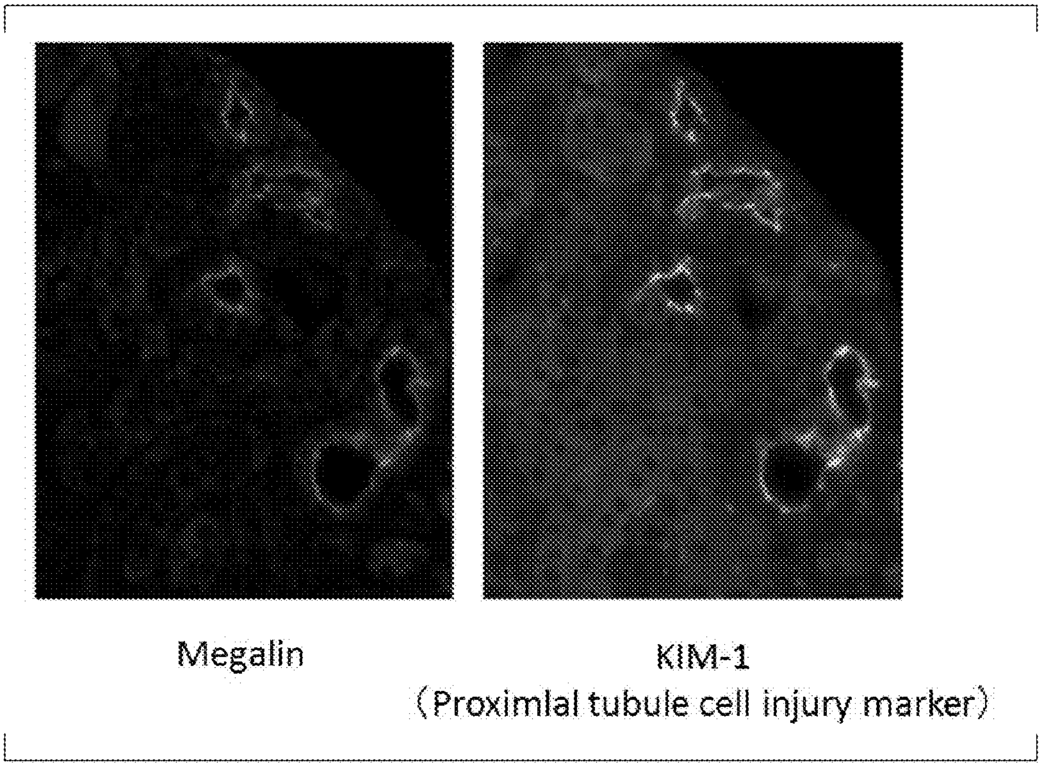
FIG. 9 is a diagram which shows proximal tubular cells (on the right) in which KIM-1, which is an injury marker of the proximal tubular cells, was expressed and proximal tubular cells (on the left) in which megalin was expressed according to a fluorescence double staining method in the proximal tubular cells in a renal-specific mosaic-type megalin knockout mouse of Reference Example 3.

As can be understood from FIG. 9, it was determined that KIM-1 was also expressed in the proximal tubular cells in which megalin, which remained without being knocked out, was expressed.

As a control, it was confirmed that KIM-1 was not expressed in the proximal tubular cells expressing megalin in the megalin knockout mice to which saline was administered using the same method.

That is, it was shown that the proximal renal tubular cell damage due to colistin largely depended on the expression of megalin and that the cilastatin or a pharmaceutically acceptable salt thereof, the suppressant, the pharmaceutical composition, and the antagonist including the cilastatin or a pharmaceutically acceptable salt thereof, which are able to prevent the binding of colistin to megalin, are an extremely effective means for suppressing (preventing or treating) cell damage caused by colistin.

Example 4

The effect of cilastatin or a pharmaceutically acceptable salt thereof of suppressing nephrotoxicity caused by colistin was investigated.

Division was made into a group in which 30 mg/kg/day of colistin was subcutaneously administered over four days to 12-week-old male C57BL/6 mice (colistin-administered group: colstin), a group in which 100 mg/kg/day of cilastatin was subcutaneously administered over four days in combination with the subcutaneous administration of 30 mg/kg/day of colistin over four days (colistin+cilastatin combination group: colstin+cilastatin), and, as a control, a group in which a physiological saline solution was subcutaneously administered over four days instead of colistin (saline group: saline), administration was performed in the same manner as the protocol of Reference Example 2 described above, after that, the kidney tissue was taken and histochemical staining (PAS staining) was performed.

Figure 10:
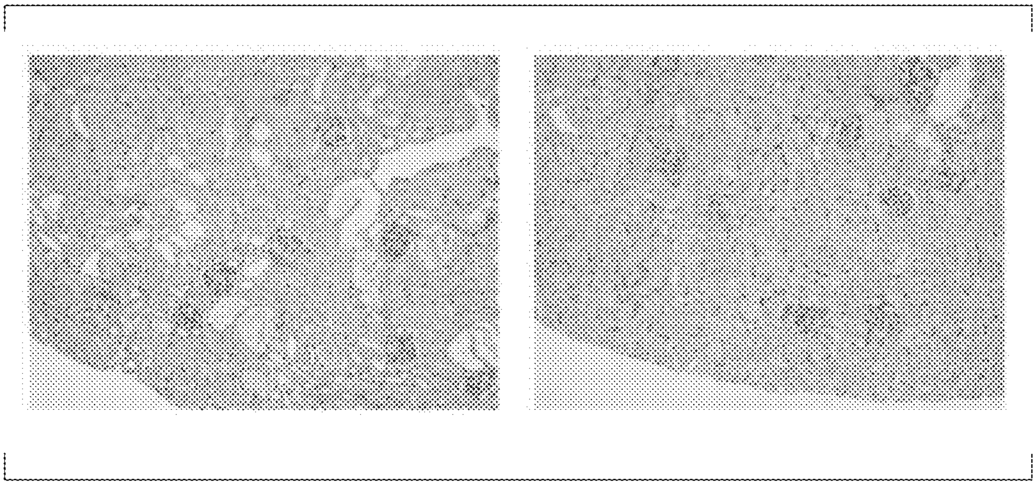
FIG. 10 is a diagram which shows the results (left) of histochemical staining (PAS staining) of kidney tissue of a colistin-administered group and the results (right) of immunohistochemical staining (PAS staining) of kidney tissue of a colistin and cilastatin combination group in Example 4.

The results are shown in FIG. 10. In the colistin administration group, the dilatation and cast formation of the tubules was observed (on the left of FIG. 10); however, in the colistin+cilastatin combination group, the dilatation and cast formation of the tubules was reduced (on the right of FIG. 10).

Furthermore, using the extracted kidney tissue, the expression of KIM-1, which is a renal tubular cell damage marker, was confirmed by Western blot. The results are shown in FIG. 11.

Figure 11:
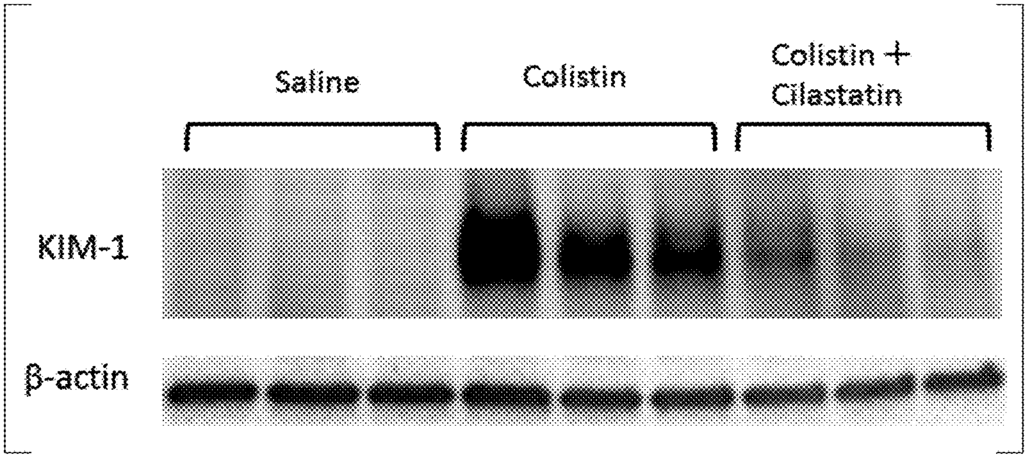
FIG. 11 is a diagram which shows the KIM-1 expression results by Western blot in renal tissue of each of a colistin-administered group, a colistin and cilastatin combination group, and a saline-administered group in Example 4.
Figure 12:
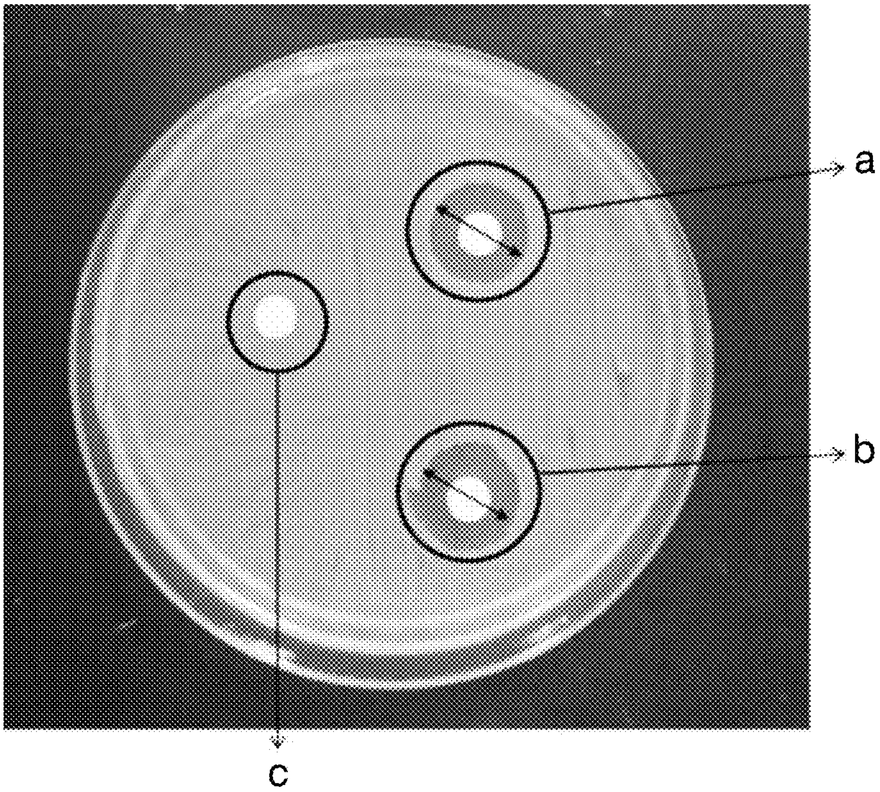
FIG. 12 is a diagram which shows the results of evaluating cilastatin interaction, which influences the anti-microbial activity of colistin and cilastatin, and the anti-microbial activity of colistin using the disk method in Reference Example 4, in which, in a case (a) of containing only colistin, a growth inhibition circle was formed (that is, there was an anti-microbial effect), in a case (b) of containing colistin and cilastatin, changes in the growth inhibition circle could not be seen, and in a case (c) of containing only cilastatin, anti-microbial activity could not be seen.

In the colistin-administered group, increased expression of KIM-1 was observed; however, in the colistin+cilastatin combination group, the expression of KIM-1 was reduced (FIG. 11). From this, it was clear that cilastatin remarkably improved the renal tubular cell damage caused by colistin, both histologically and biochemically.

Reference Example 4

An ATCC25922 strain (*E. coli* standard strain) was cultured for 20 hours using Mueller Hinton agar (MHA) and then the cultured colonies were suspended in saline and adjusted to obtain a solution equivalent to McFarland turbidity standard 0.5. After uniformly coating and drying the microbial solution on the MHA, 10 μg of colistin, cilastatin, and colistin and cilastatin were each added to 6 mm Whatman filter paper discs, disposed at equal intervals on the MHA described above, and cultured for 20 hours at 37° C., and the blocking circles were compared. The results are shown in FIG. 11. In the cilastatin-containing disk, a blocking circle was not formed and anti-microbial activity was not exhibited. In addition, the colistin-containing disk and the colistin and cilastatin-containing disk each had a blocking circle diameter of 13.5 mm. As a result, it was determined that cilastatin has no anti-microbial activity and does not affect the anti-microbial activity of colistin.

INDUSTRIAL APPLICABILITY

The cilastatin or a pharmaceutically acceptable salt thereof according to the present invention, and the suppressant, the pharmaceutical composition, and antagonist, which include the cilastatin or a pharmaceutically acceptable salt thereof as an active component can suppress cell damage induced by various types of megalin ligand and diseases derived therefrom, thus the present invention is extremely useful in terms of industrial application.

The invention claimed is:

1. A formulation which combines cilastatin or a pharmaceutically acceptable salt thereof with at least one active component which is selected from the group consisting of colistin, colistin methanesulfonate, and pharmaceutically acceptable salts thereof, wherein an amount of the cilastatin or the pharmaceutically acceptable salt thereof is 0.5 parts by mass to 100 parts by mass with respect to 1 part by mass of the active component, and the combined formulation is for use simultaneously, separately, or at time intervals.

2. A pharmaceutical composition, comprising:

cilastatin or a pharmaceutically acceptable salt thereof;

at least one active component which is selected from the group consisting of colistin, colistin methanesulfonate, and pharmaceutically acceptable salts thereof; and a pharmaceutically acceptable carrier, wherein the cilastatin or the pharmaceutically acceptable salt thereof is included in an amount of 0.5 parts by mass to 100 parts by mass with respect to 1 part by mass of the active component.

3. An anti-microbial agent, comprising:

cilastatin or a pharmaceutically acceptable salt thereof;

at least one active component which is selected from the group consisting of colistin, colistin methanesulfonate, and pharmaceutically acceptable salts thereof; and a pharmaceutically acceptable carrier, wherein the cilastatin or the pharmaceutically acceptable salt thereof is included in an amount of 0.5 parts by mass to 100 parts by mass with respect to 1 part by mass of the active component.

4. The anti-microbial agent according to claim 3, wherein the cilastatin or the pharmaceutically acceptable salt thereof is included in an amount of 1.5 parts by mass to 3 parts by mass with respect to 1 part by mass of the active component.

5. A pharmaceutical kit, comprising:

cilastatin or a pharmaceutically acceptable salt thereof in a first compartment; and at least one megalin ligand which is selected from the group consisting of colistin, colistin methanesulfonate, and pharmaceutically acceptable salts thereof in a second compartment, wherein the first compartment contains 0.5 parts by mass to 100 parts by mass of the cilastatin or the pharmaceutically acceptable salt thereof with respect to 1 parts by mass of the megalin ligand in the second compartment.

6. A method for treating or preventing infections caused by at least one multidrug-resistant Gram-negative bacteria selected from the group consisting of *Pseudomonas aeruginosa, Acinetobacter* spp., *Escherichia coli, Citrobacter* spp., *Enterobacter* spp., and *Klebsiela* spp., the method comprising:

administering to a subject in need thereof a therapeutically effective amount of cilastatin or a pharmaceutically acceptable salt thereof in combination with a therapeutically effective amount of colistin, colistin methanesulfonate, or pharmaceutically acceptable salts thereof, wherein 0.5 parts by mass to 100 parts by mass of the cilastatin or the pharmaceutically acceptable salt thereof is administered with respect to 1 part by mass of the colistin, the colistin methanesulfonate, or the pharmaceutically acceptable salts thereof.

7. The pharmaceutical composition according to claim 2, wherein the cilastatin or the pharmaceutically acceptable salt thereof is included in an amount of from 0.1 mass % to 1 mass %.

8. The pharmaceutical composition according to claim 2, wherein the pharmaceutically acceptable carrier comprises at least one selected from the group consisting of distilled water, a lidocaine hydrochloride solution, saline, a glucose aqueous solution, ethanol, polyethylene glycol, propylene glycol, an aqueous solution of citric acid, an aqueous solution of sodium citrate, and an electrolyte solution.

9. The method according to claim 6, wherein the at least one multidrug-resistant Gram-negative bacteria includes multidrug-resistant *Pseudomonas aeruginosa.*

10. The method according to claim 6, wherein the at least one multidrug-resistant Gram-negative bacteria includes multidrug-resistant *Acinetobacter* spp.

11. The method according to claim 6, wherein the at least one multidrug-resistant Gram-negative bacteria includes multidrug-resistant *Klebsiella* spp.

* * * * *